(12) United States Patent
Ajgaonkar et al.

(10) Patent No.: US 7,869,054 B2
(45) Date of Patent: Jan. 11, 2011

(54) POLARIZATION INSENSITIVE MULTIPLE PROBE

(75) Inventors: Mahesh U. Ajgaonkar, Buda, TX (US); Cristian Toma, Orlando, FL (US)

(73) Assignee: Medeikon Corporation, Ewing, NJ (US)

( * ) Notice: Subject to any disclaimer, the term of this patent is extended or adjusted under 35 U.S.C. 154(b) by 642 days.

(21) Appl. No.: 11/753,945

(22) Filed: May 25, 2007

(65) Prior Publication Data

US 2007/0285669 A1 Dec. 13, 2007

Related U.S. Application Data

(60) Provisional application No. 60/803,264, filed on May 26, 2006.

(51) Int. Cl.
*G01B 11/02* (2006.01)
(52) U.S. Cl. ...................................... 356/491
(58) Field of Classification Search ................. 356/491, 356/492
See application file for complete search history.

(56) References Cited

U.S. PATENT DOCUMENTS

| | | |
|---|---|---|
| 4,941,744 A | 7/1990 | Yokokura et al. |
| 5,060,312 A | 10/1991 | Delavaux |
| 5,710,630 A | 1/1998 | Essenpreis et al. |
| 5,951,482 A | 9/1999 | Winston et al. |
| 6,063,093 A | 5/2000 | Winston et al. |
| 6,193,676 B1 | 2/2001 | Winston et al. |
| 6,226,089 B1 | 5/2001 | Hakamata |
| 6,408,349 B1 | 6/2002 | Castellano |
| 6,419,484 B1 | 7/2002 | Dasilva et al. |
| 6,657,727 B1 | 12/2003 | Izatt et al. |
| 6,816,261 B2 | 11/2004 | Patel et al. |
| 6,842,639 B1 | 1/2005 | Winston et al. |
| 6,943,881 B2 | 9/2005 | Wang |
| 6,970,732 B2 | 11/2005 | Winston et al. |
| 7,184,148 B2 | 2/2007 | Alphonse |
| 2005/0254058 A1 | 11/2005 | Alphonse |
| 2005/0254060 A1 | 11/2005 | Alphonse |
| 2007/0236700 A1 * | 10/2007 | Yun et al. .................. 356/491 |

* cited by examiner

*Primary Examiner*—Patrick J Connolly
(74) *Attorney, Agent, or Firm*—Pepper Hamilton LLP

(57) ABSTRACT

An apparatus for determining a polarization-insensitive interferometric signal and a birefringence for a sample and methods for using such an apparatus to characterize the sample are proved herein. Such apparatuses may generally be designed to eliminate birefringence associated with the apparatus itself, collect data from the sample using light in both orthogonal states, and determine the interference birefringence associated with the collected data.

32 Claims, 9 Drawing Sheets

POLARIZATION INSENSITIVE MULTIPLE PROBE

CROSS REFERENCE

This application claims priority to and benefit of U.S. Provisional Application No. 60/803,264 entitled "Polarization insensitive Multiple Probe" filed on May 26, 2006, the entire contents of which is hereby incorporated by reference.

BACKGROUND

Interferometry is a well known technique for examining a sample using interference between light backscattered from a sample, and light from a reference source. Low-Coherence Interferometry (LCI) and Optical Coherence Tomography (OCT) are examples of methods for examining a sample using backscattered light. LCI is an optical technique that relies on "coherence gating" to provide precise axial positioning of an object in the direction of light propagation. By focusing the light in a sample, a transverse resolution may also be obtained (perpendicular to the optical beam), thus allowing for the collection of information from a finite volume for imaging or optical characterization purposes. OCT is an imaging technique which allows high resolution observation and characterization of tissue microstructure imaging with resolution on the order of micros. This technique measures detailed changes with a few millimeters of a non-transparent tissue structure. One drawback of OCT imaging is the time to acquire a large number of data points necessary to obtain an image over a sufficient area.

Interferometery data is provided by an interferometer which may be configured in any of a number of ways to create various interferometers including, but not limited to, an autocorrelator, a Fizeau interferometer, a Mach Zehnder interferometer, and a Michelson interferometer. FIG. 1 illustrates an exemplary LCI or OCT probe system interferometer that includes a light source 100 which provides light that is propagated through one or more waveguides coupled to a splitter 102 which redirects light from the light source 100 into waveguides that make up at least one reference arm 107 and one or more sample arms 106. In embodiments including more than one sample arm, as shown in FIG. 1, a second splitter 109 or a multiple-output optical switch may be optically coupled to the first splitter 102 to direct light from the light source 100 into a plurality of sample arts 106. In operation, illuminated light from the light source 100 is propagated through the sample arm 106 and the reference arm 107 and is emitted at the distal ends of the sample arm 106 and the reference arm 107. Backscattered light is then collected by the distal ends of the sample arm 106 and the reference arm 107 and propagated back through the sample arm 106 and the reference arm 107 in the opposite direction of the illuminated light. In FIG. 1, light emitted and backscattered light returning to the sample arms 106 are represented by dashed line arrows. Light from the sample arm 106 and the reference arm 107 are then recombined, and a detector 108 is used to convert a light signal from the combined backscattered light into an electronic signal which is passed to a receiver 110 whose output can be obtained and/or measured by a Digital Acquisition Board and a processor 118. In various embodiments, interference between the signal obtained from reference arm and signal from the sample arm may be measured and utilized to characterize morphology, physical nature, composition, and various other properties of a sample in proximity to the distal end of the probe using known methods (See, for example, U.S. patent application Ser. No. 11/039,987, published as 2005/0254060, entitled "Low Coherence Inteferometry for Detecting Plaques" hereby incorporated by reference in its entirety).

Interference may occur between light components having the same polarization. The waveguides 116 of interferometers, as illustrated in FIG. 1, are typically optical fibers which propagate light in two orthogonal polarization states, p-polarization and s-polarization. In many cases, light from the light source 100 injected into optical fibers is polarized to eliminate one of the polarization states. However, as light travels through the optical fiber the polarization state of the light in the optical fiber may change as a result of, for example, birefringence in the optical fiber, fiber handling and/or environmental conditions. Therefore, if light is introduced in the s-polarization state, a certain amount of the light detected may be randomly coupled into the p-polarization state, and if a single detector is used to generate an electronic signal, the amplitude of the signal can vary producing variability in the measurements. In addition, the sample under test itself may be birefringent, causing partial rotation of light propagating through it.

Birefringence caused by passage of light through an optical fiber may be mitigated by creating an interferometer that is polarization insensitive. The interferometer must be initialized or balanced prior to use with a sample that is birefringent. Once the interferometer is balanced, any additional birefringence observed in the data obtained from the backscattered light signal may be attributable to birefringence of the sample. Measured birefringence from the sample may provide significant insight into the characteristics of the sample. For instance, birefringence caused by biological tissues or "tissue birefringence" is a common phenomenon in biological samples examined using LCI or OCT interferometers and mapping these birefringence properties may provide insight into the health of the tissue being examined. Tissue birefringence can be caused by a number of fibrous tissue components, such as, collagen and elastin fibers which arrange themselves in highly anisotropic structures, such as, for example, tendons, ligaments, skin, blood vessels and structures of the eye, brain, and spinal cord and the like. Therefore, without wishing to be bound by theory, difference in the birefringence properties of biological samples can be used to detect disturbances in the regularity of such structures indicative of diseased tissue. For example, birefringence data may be used to determine the depth of a burn on the skin or locate fibrous caps in atherosclerotic vascular tissue.

Embodiments of the invention described herein include receiver architectures designed to eliminate birefringence from an optical signal of an interferometer so that birefringence data from a sample may be obtained.

SUMMARY

The invention described herein is generally directed to an apparatus including a polarization controller; a polarization splitter optically coupled to the polarization controller; an optical coupler optically coupled to either one of the polarization controller; or the one polarization splitter; first and second detectors optically coupled to either one of the polarization splitter or the optical coupler; and a balanced detector electrically connected to at least one of the first and second detectors.

In some embodiments, the apparatus may further include a second polarization controller optically coupled to the optical coupler, and in other embodiments, the apparatus may further include a second polarization splitter optically coupled to the second polarization controller. In still other embodiments, the apparatus may further include third and fourth detectors optically coupled to the second polarization splitter. In yet other embodiments, the apparatus may further include a second balanced detector electrically connected to the second and fourth detectors.

In certain embodiments, the apparatus may further include a second polarization controller optically coupled to the optical coupler, and in some embodiments, the apparatus may include a second polarization splitter and the at least one of the third and fourth detectors may be embodiments, the apparatus may further include third and fourth detectors optically coupled to the second polarization splitter and the at least one of the third and fourth detectors may be electrically connected to the balanced detector. In still other embodiments, the apparatus may further include a second balanced detector electrically connected to at least one of the third and fourth detectors and the at least one of the third and fourth detectors may be electrically connected to the balanced detector.

In other embodiments, the apparatus may further include a second balanced detector electrically connected to at least one of the first and second detectors, and in still other embodiments, the apparatus may further include third and fourth detectors, wherein at least one of the third and fourth detectors may be electrically connected to the balanced detector.

Various embodiments of the apparatus also include a second polarization splitter optically coupled to the optical coupler. In some embodiments, the apparatus may further include a second optical coupler optically coupled to the polarization splitter and the second optical coupler may be optically coupled to the polarization splitter. In other embodiments, the apparatus may further include third and fourth detectors optically coupled to the second optical coupler. In still other embodiments, the apparatus may further include a second balanced detector electrically connected to at least one of the third and fourth detectors.

The apparatus may further include a second optical coupler optically coupled to the polarization splitter.

In some embodiments, the apparatus may further include an optical circulator optically coupled to at least one of the optical coupler and the polarization splitter, and the apparatus may further include a second optical circulator optically coupled to at least one of the following the optical coupler and a second polarization splitter which is optically coupled to the optical coupler.

Embodiments of the invention also include a system including an interferometer; and an apparatus optically coupled to the interferometer, wherein the apparatus including a polarization controller; a polarization splitter optically coupled to the polarization controller; an optical coupler optically coupled to one of, the polarization controller and the one polarization splitter; first and second detectors optically coupled to one of the polarization splitter and the optical coupler; and a balanced detector electrically connected to at least one of the first and second detectors.

Some embodiments of the system further including a first optical circulator optically coupled to a reference arm of the interferometer; and a second optical circulator optically coupled to a sample arm of the interferometer, and other embodiments the system the first optical circulator may be optically coupled to one of the optical connector and the polarization controller. In still other embodiments of the system the second optical circulator may be optically coupled to one of the optical connector and a second polarization splitter which is optically coupled to the optical coupler.

The system of various embodiments may further include an analog to digital converter electrically connected to the apparatus and/or a computing device in communication with the analog to digital converter, wherein the computing device includes at least one of the following: a polarization-insensitive module configured to determine a polarization-insensitive envelope based on an output signal of the apparatus and a birefringence-sensitive module configured to determine a birefringence envelope based on an output signal of the apparatus. In still other embodiments, the system may include a display device in communication with the computing device.

Embodiments of the invention further include a method for determining a characteristic of a sample using an interferometer, the method including the steps of illuminating the sample via the interferometer; illuminating a mirror associated with the interferometer; collecting backscattered light from the sample to provide a first reflected component; collecting reflected light from the mirror to provide a second reflected component; controlling polarization of the first and second reflected components; determining a p-polarization component and a s-polarization component for each of the first and second reflected components; determining a difference between the p-polarization components and a difference between the s-polarization components; and determining a birefringence sensitive signal based on the difference between the p-polarization components and the difference between the s-polarization components.

In various embodiments, controlling the polarization may be controlling the polarization such that, when the sample is absent the p-polarization component and the s-polarization component of the first reflected component are of equal intensity and the p-polarization component and the s-polarization component of the second reflected component are of equal intensity. In other embodiments, controlling the polarization may be controlling an optical path length in the interferometer.

In some embodiments of the method, determining the p-polarization component and the s-polarization component for each of the first and second reflected components includes optically combining the first and second reflected components; controlling the polarization of the combined components; and splitting the first and second reflected components into their respective p-polarization and s-polarization component. In other embodiments, determining the p-polarization component and the s-polarization component for each of the first and second reflected components includes controlling the polarization of the second reflected component; and splitting the first and second reflected components into their respective p-polarization and s-polarization components, and in still other embodiments, determining a difference between the p-polarization components and a difference between the s-polarization components includes generating electrical signals representative of the respective p-polarization and s-polarization components of the first and second reflected components. In yet other embodiments, determining a difference between the p-polarization components and a difference between the s-polarization components includes optically combining the p-polarization components of the first and second reflected components; optically combining the s-polarization components of the first and second reflected components; and generating electrical signals representative of the respective p-polarization and s-polarization components of the first and second reflected components.

In certain embodiments, the method further includes the step of determining a characteristic of the sample based on the birefringence sensitive signal, and in other embodiments, the method includes the step of determining a polarization-insensitive signal associated with the sample.

The method of various embodiments may also include the steps of determining the polarization insensitive signal by determining a p-envelope based on the difference between the p-polarization components of the first and second reflected components and determining a s-envelope based on the difference between the s-polarization components of the first and second reflected components. In some embodiments, the p-envelope and the s-envelope may be determined over a range of optical pathlengths by adjusting a pathlength of the interferometer.

In particular embodiments, determining the polarization-insensitive signal includes determining a value for the expression:

$$20 \log\sqrt{env(P)^2 + env(S)^2} \text{ (dB), and}$$

In other embodiments, determining the birefringence sensitive signal comprises determining a value for the expression:

$$20\log\left(\frac{env(P)}{env(S)}\right)\text{(dB)},$$

wherein env(P) is determined based on the difference between the p-polarization components of the first and second reflected components, and wherein env(s) is determined based on the difference between the s-polarization components of the first and second reflected components.

DESCRIPTION OF DRAWINGS

The file of this patent contains at least one drawing executed in color. Copies of this patent with color drawing(s) will be provided by the Patent and Trademark Office upon request and payment of necessary fee.

For a better understanding of the disclosure and to show how the same may be carried into effect, reference will now be made to the accompanying drawings. It is stressed that the particulars shown are by way of example only and for purposes of illustrative discussion of the preferred embodiments of the present disclosure only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. In the accompanying drawings.

DETAILED DESCRIPTION

Figure 1:
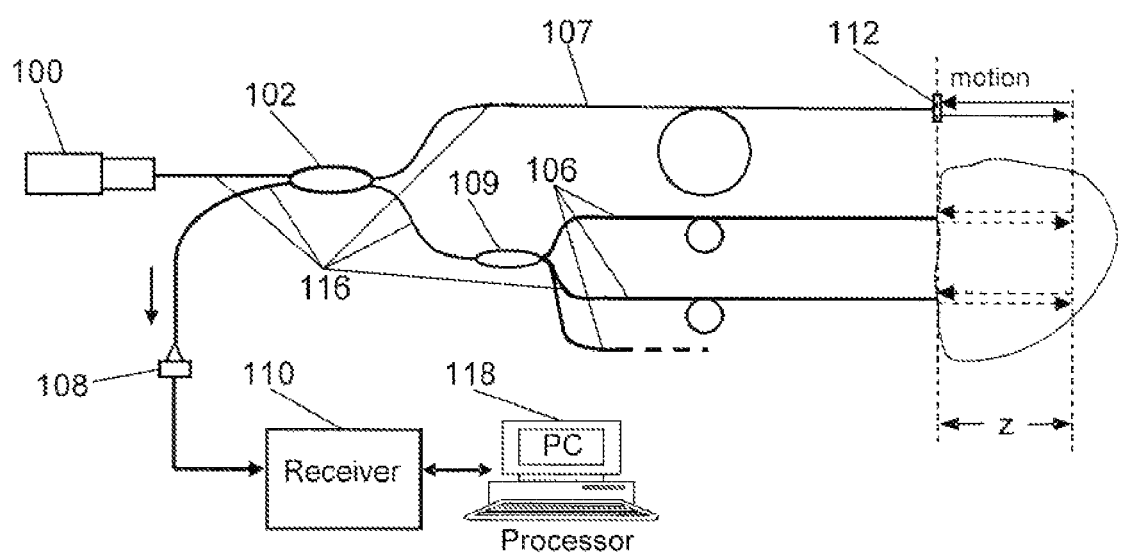
FIG. 1 illustrates embodiments of a LCI or OCT probe system.

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

It must also be noted that as used herein and in the appended claims, the singular forms "a", "an", and "the" include plural reference unless the context clearly dictates otherwise. Thus, for example, reference to a "lesion" is a reference to one or more lesions and equivalents thereof know to those skilled in the art, and so forth. Unless defined otherwise, all technical and scientific terms used herein have the same meanings as commonly understood by one of ordinary skill in the art. Although any methods and materials similar or equivalent to those described herein can be used in the practice or testing of embodiments of the present invention, the preferred methods, devices, and materials are now described.

The methods as described herein for use contemplate prophylactic use as well as curative use in therapy of an existing condition. As used herein, the term "about" means plus or minus 10% of the numerical value of the number with which it is being used. Therefore, about 50% means in the range of 45%-55%.

"Optional" or "optionally" means that the subsequently described structure, event or circumstance may or may not occur, and that the description includes instances where the event occurs and instances where it does not.

Generally speaking, the term "tissue" refers to any aggregation of similarly specialized cells which are united in the performance of a particular function. For example, the term "tissue" may refer to tissue that makes up an organ on which a lesion may occur.

The invention generally described herein is directed to an interferometer system having a receiver capable of eliminating birefringence caused by the interferometer itself such that birefringence data from a sample may be obtained, various receivers having an architecture that allows for the elimination of birefringence caused by an interferometer and collection of birefringence data from a sample, and methods for making and using a receiver to eliminate birefringence from an interferometer and collecting birefringence data from a sample.

In embodiments of the invention, a polarization-insensitive interferometer system may be achieved by obtaining a spatially-resolved signal whose amplitude relates only to the birefringence of the sample. In other embodiments, a standard, polarization-insensitive interferometric signal having a magnitude proportional to the spatially resolved reflectivity of a sample may be obtained in which birefringence effects have been mitigated or eliminated from the signal. In yet further embodiments, both a standard interferometric signal and a birefringence signal from a sample may be obtained simultaneously, and in certain embodiments, the two signals may be co-registered such that they can be compared, data sample to data sample, without additional processing.

Figure 2:
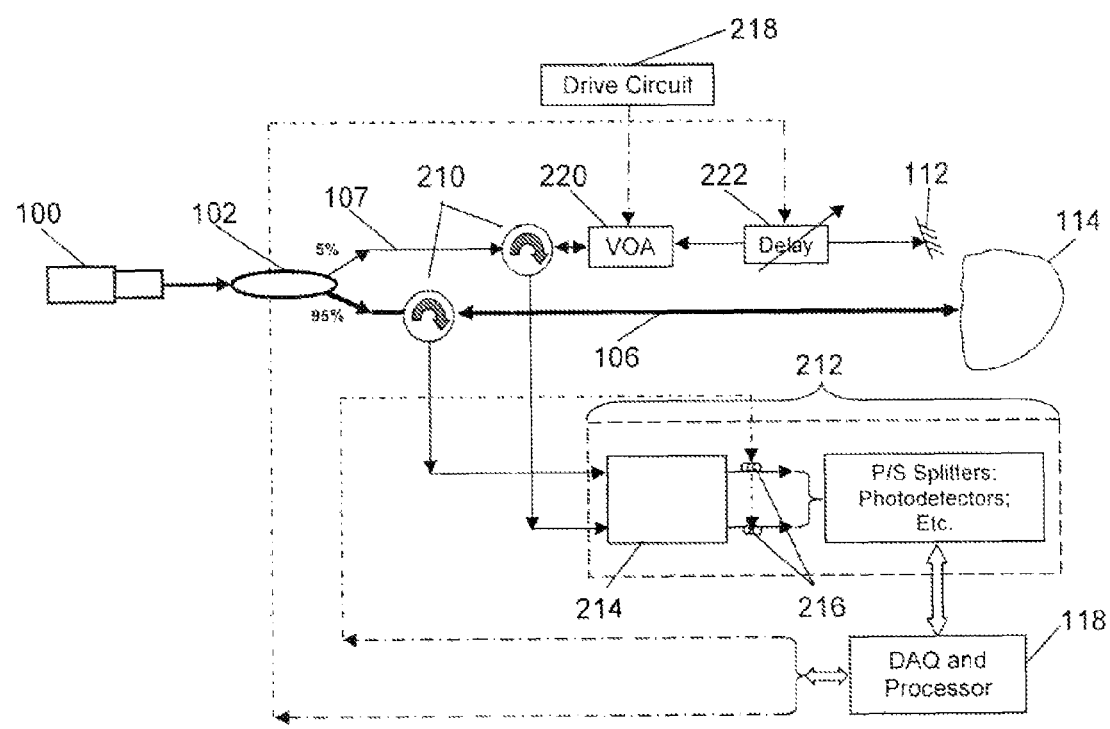
FIG. 2 illustrates embodiments of a LCI or OCT probe system configured to collect polarization-insensitive interferometric data and birefringence-sensitive data.

A polarization-insensitive system with birefringence-sensitive signal may be obtained using an LCI or OCT probe system known in the art, such as, for example, that of FIG. 1, having a receiver architecture devised to eliminate device-produced birefringence. For example, FIG. 2 illustrates an embodiment of an LCI or OCT probe system that has been configured to eliminate birefringence caused by the propagation of light through a probe device and determine birefringence of a sample. In FIG. 2, a light source 100 is optically coupled to a splitter 102 which directs light from the light source 100 into at least one reference arm 107 and one or more sample arms 106. In particular embodiments, the light may be split disproportionately using, for example, a high ratio optical splitter, so a greater fraction of the light from the light source 100 is directed to, for example, one or more sample arms 106. A second splitter, not depicted, may also be used to direct light from the light source 100 into a plurality of sample arms 106. As in the interferometer of FIG. 1, light is propagated through the sample and reference arms 106, 107, emitted from the distal ends of the sample and reference arms 106, 107, and backscattered light is collected from the distal ends of the sample and reference arms 106, 107. Optical circulators 210 positioned between the splitter 102 and the distal ends of the sample and reference arms 106, 107 may be used to redirect backscattered light from the sample and reference arms 106, 107 to a receiver 212. Therefore, reflected light returning from the sample arms 106 and reference arms 107 are not recombined at the splitter. A receiver 212 as embodied herein may include means for determining polarization and/or adjusting the polarization of light the interferometer and may include, for example, one or more optical couplers 214, polarization controllers 216, polarization sensitive splitters, photodetectors, optical circulators, data acquisition boards, processors, and the like. According to various embodiments, the optical circulators 210 may be considered as a portion of the receiver 212. In some embodiments, the receiver 212 may also include output devices (signified by dashed lines) which may control and/or automatically adjust one or more components of the interferometer, such as a drive circuit 218, variable optical attenuator (VOA) 220, or optical delay 222 associated with a reference 107 or sample arm 106, or one or more component of the receiver 212, such as, but not limited to, a polarization controller 216.

Figure 3:
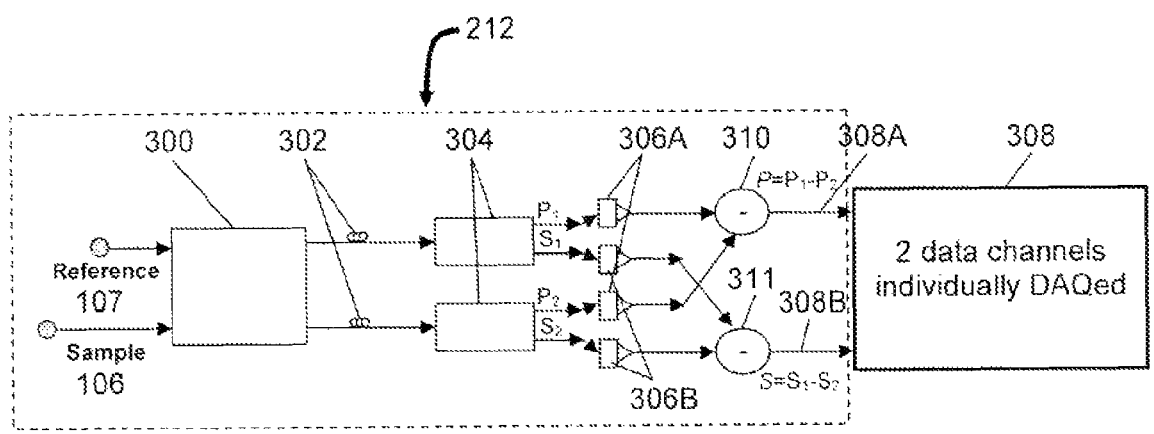
FIG. 3 illustrates an embodiment of the receiver of the system of FIG. 2.

The receiver 212 may be configured to provide backscattered light from the sample and reference arms 106, 107 that is split into its orthogonal polarization sates, p-polarization (hereinafter "p") and s-polarization (hereinafter "s"), prior to detection. In an exemplary embodiment of the receiver 212 as illustrated in FIG. 3, reference light from a reference arm 107 and backscattered light from a sample arm 106 enter the receiver 212 and are combined by an optical coupler 300. In some embodiments, light leaving the optical coupler 300 may be adjusted such that each of the polarization states of light exiting the optical coupler 300 are equal. This may be accomplished by passing light exiting the optical coupler 300 through a component capable of adjusting the input light such as, for example, a polarization controller 302. The light may then be passed through a polarization splitter 304, such as, for example, a P/S splitter, that separates input light into its p and s orthogonal states, and detectors for the p component 306A and detectors for the s component 306B may be used to detect each p and s component exiting the splitter 304. The detectors 306A, 306B, generate analog output signals that are representative of the respective p and s components of the detected light. The analog signal representative of the p components (i.e. $P_1$ and $P_2$) are input into balanced detectors 310 and the analog signal representative of the s components (i.e. $S_1$ and $S_2$) are input into a separate balanced detectors 311. The balanced detectors 310, 311 generate outputs that reflect the difference between the respective p and s components (i.e., $P=P_1-P_2$ and $S=S_1-S_2$). The output of the balanced detectors 310, 311 may than be converted to a digital signal using for example, a digital acquisition board (DAQ) 308 or the like, and in certain embodiments, the data may be acquired by the DAQ via two data channels and, one data channel for p data 308A and a separate data channel for s data 308B, as illustrated in FIG. 3. The digital data may be stored or transferred directly to a processor. This data may then be used to determine the polarization-insensitive interferometric signal, and the birefringence caused by the sample.

Figure 4:
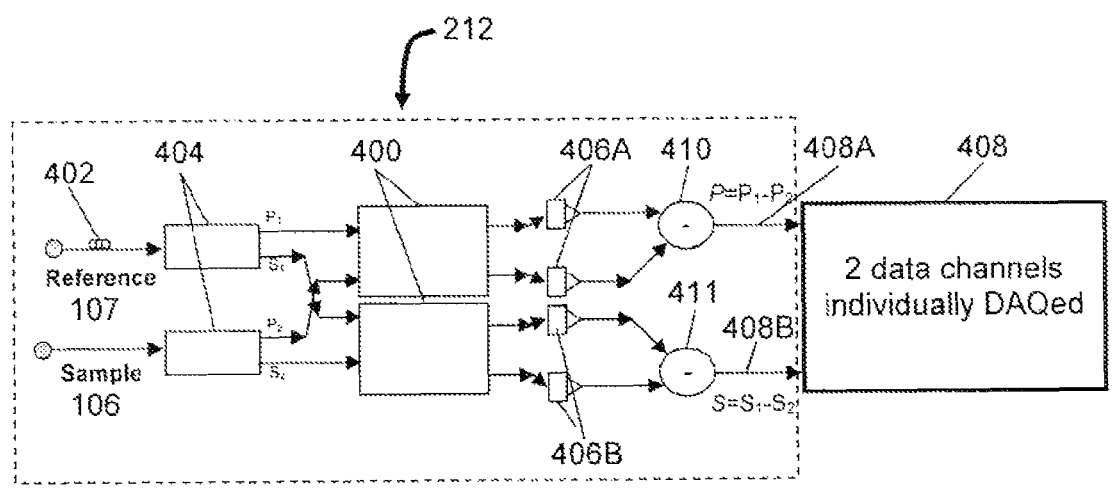
FIG. 4 illustrates an embodiment of the receiver of the system of FIG. 2.

In another embodiment, polarization controllers may be used to adjust the polarization of input light from either the reference arm, the sample arm or both before the signals are split or combined, and in one embodiment, as illustrated in FIG. 4, a single polarization controller 402 is used only on incoming light from the reference arms. In some embodiments, also illustrated in FIG. 4, the p and s state light are split using a polarization splitter 404 before light from the reference and sample arms are combined by an optical coupler 400. Therefore, only the p state light from the reference and sample arms or only the s state light from the reference and sample arms are combined. The combined signals are then detected using detectors for the p component 406A and detectors for the s component 406B for each p and s component exiting the optical coupler 400. The p and s components of the analog signal generated by each detector 406A, 406B may be detected by balanced detectors 410, 411 by there orthogonal state, and the output of the balanced detectors 408A, 408B reflect the difference between the respective p and s components (i.e., $P=P_1-P_2$ and $S=S_1-S_2$) as described above. The output from the balanced detectors 410, 411 may be converted to a digital signal 408, acquired, stored or transferred to a processor, and used to determine the polarization-insensitive interferometric signal, and the birefringence caused by the sample, as described above.

Embodiments of the invention also include methods for using receivers having architectures as illustrated in FIGS. 3 and 4. In various embodiments, the interferometer system may be initialized by leaving the sample art 106 free in air, or immersing it in water/saline media and away from scattering surfaces. One or more polarization controllers 302, 402 may be adjusted to produce equal optical power from the sample and reference signal from each P and S output of the polarization splitter 304, 404. Therefore, in the signal detected, $P_1=S_1=P_2=S_2$. This may be accomplished using polarization controllers 302 that act on combined light from the sample and reference arms 106, 107, as illustrated in FIG. 3, or this may be accomplished using a single polarization controller 402 on either light from the sample or reference arm 106, 107 entering the receiver, as illustrated in FIG. 4 where a single polarization controller 402 is used to control the polarization state of light from the reference arm 107. Without wishing to be bound by theory, initialization of the receiver 212 essentially removes birefringence resulting from the probe itself. Therefore, birefringence from the probe does not contribute to the optical signal obtained during sample interrogation.

In still other embodiments, the overall power of the optical signal delivered to the sample or reference arm 106, 107 or returning from the sample or reference 106, 107 may be adjusted using, for example, a VOA 220 associated with either sample or reference arm 106, 107, as illustrated in FIG. 2 where a VOA 220 associated with the reference arm 107. In such embodiments, the VOA 220 may be adjusted with the polarization controller 302, 402 during initialization. In other embodiments, the VOA 220 may be adjusted throughout scanning to provide equal power from the reference or sample signal at all times. In certain embodiments, the VOA 220 may be controlled automatically by a processor 118 that is collecting and analyzing data collected by the interferometer based on the incoming data.

Following initialization, a sample may be scanned and backscattered light may be collected from the sample 114 as is generally known in the art. In particular, the signal collected from various depths within the sample 114 may be obtained by altering the optical path length of the reference light by changing the length of the reference arm 107. Scanning may be accomplished by any method, for example, an adjustable or variable time delay 222 associated with the light propagation in the reference arm 107 may be used, the optical path length of the reference arm 107 may be changed using, for example, a movable mirror 112, optical stretcher, piezoelectric stretcher and the like, or the index of refraction of a portion of the reference arm may be changed. In the exemplary embodiment of FIG. 2, a scanning delay line 222 may be used to adjust the length of the reference arm 107 over a given distance. The scanning delay line 222 may be controlled by a processor 118 that is collecting and analyzing data collected from the sample 114. Although only one variable optical attenuator 220 and one delay device 222 are shown being associated with the reference arm 107 in FIG. 2, it is understood that the interferometer may include any number of variable optical attenuators 220 and delay devices 222, and each sample arm 106 may have a variable optical attenuator and a delay device associated therewith.

During scanning, the length of the reference arm 107 is increased, and the probed depth of the sample 114 is increased to a depth corresponding with the length of the reference arm 107. Therefore, the measurement of the peak gating function give the amplitude of the profile of the signal as a function of depth, and the data collected during scanning can be used to identify irregular structures up to a specific depth corresponding with the maximum length of the reference arm 107 in the sample 114. The length of the reference arm 107 may be adjusted over any number of increments during scanning. For example, a "quick" scan may be performed by adjusting the length of the reference arm 107 by large increments, and a continuous scan may be carried out using very small increments and used to precisely define structures identified using a quick scan.

Figure 5:
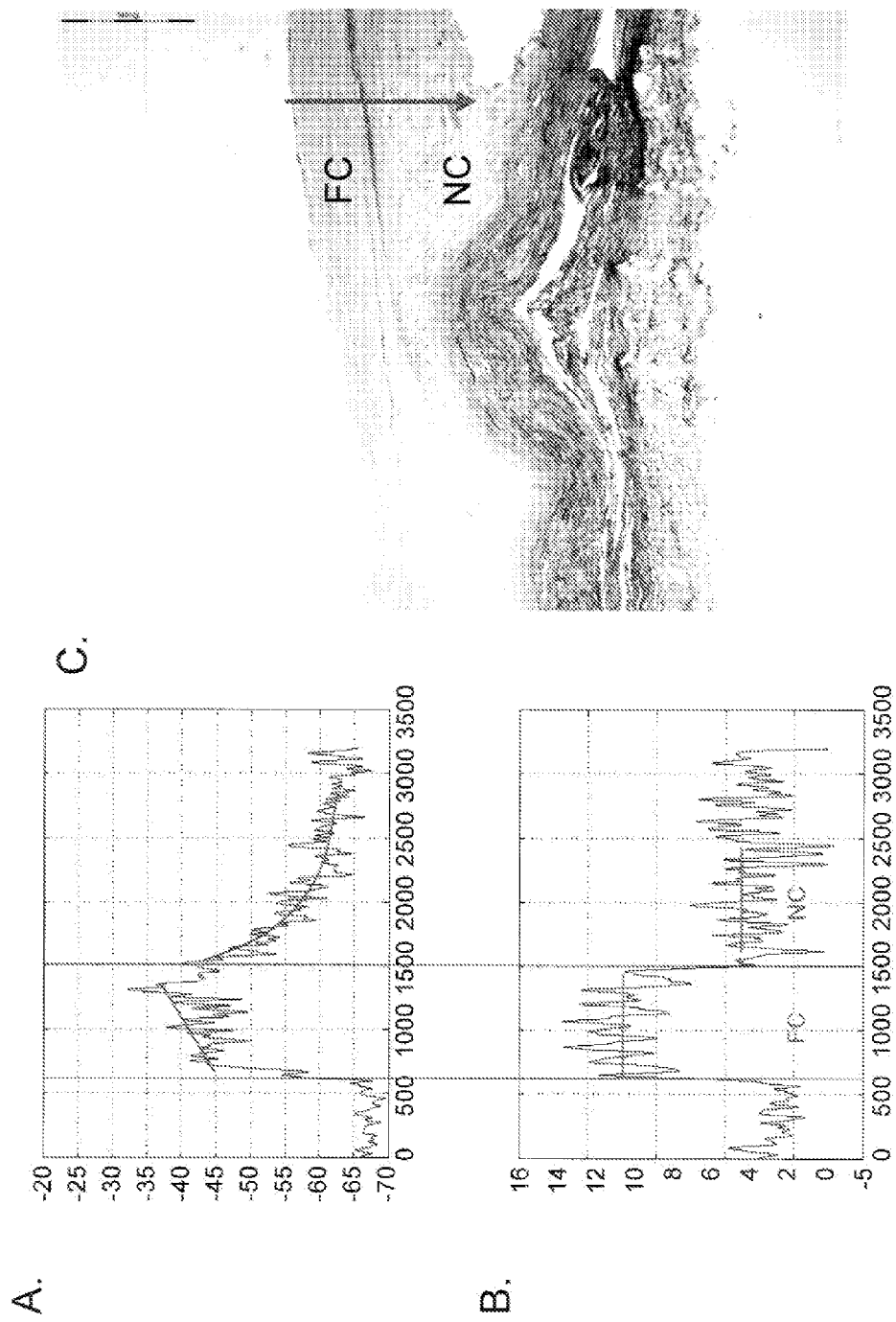
FIG. 5 shows exemplary data collected from aortic tissue using an interferometer, as embodied herein, configured to collect polarization-insensitive interferometric data and birefringence-sensitive data.
Figure 6:
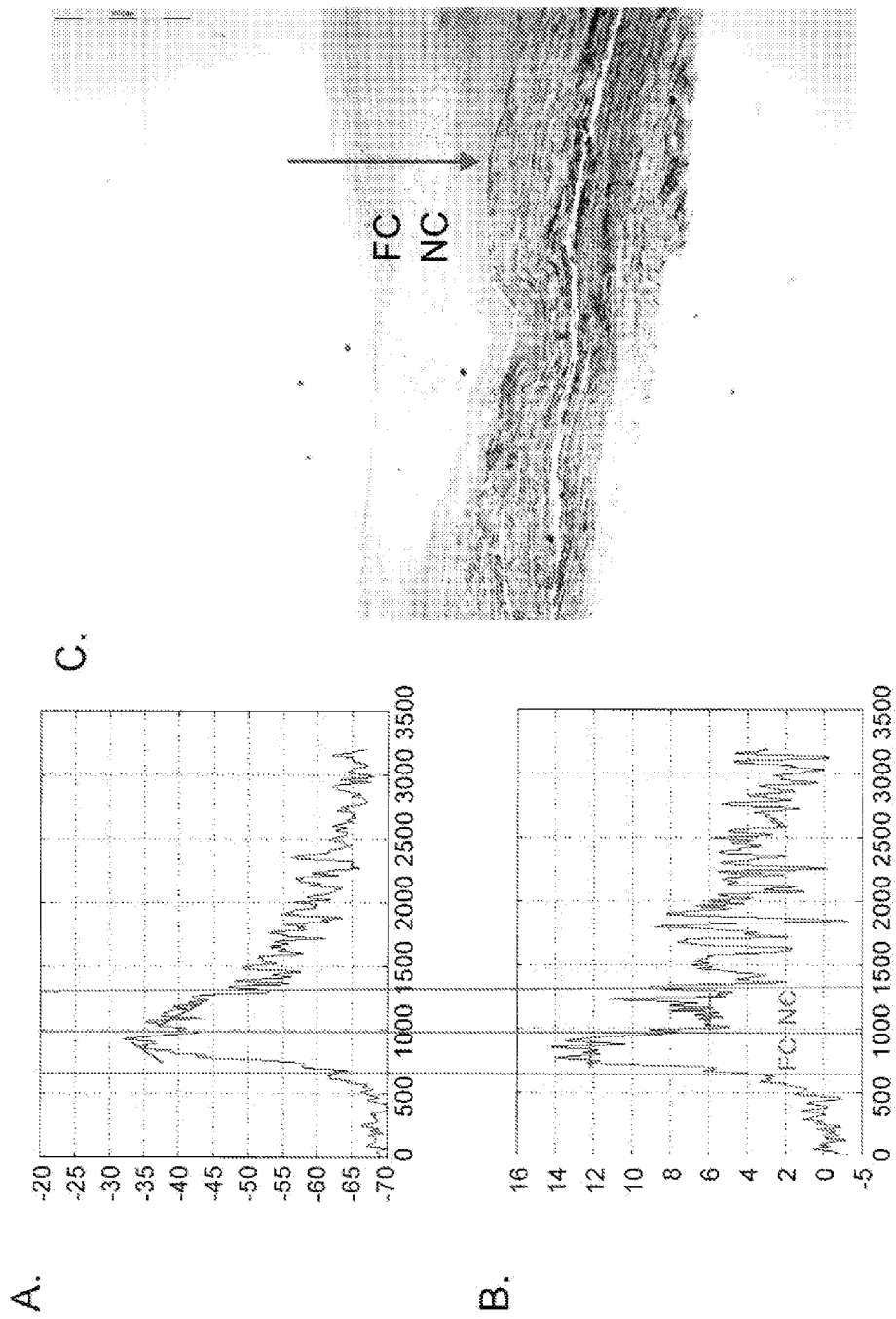
FIG. 6 shows exemplary data collected from aortic tissue using an interferometer, as embodied herein, configured to collect polarization-insensitive interferometric data and birefringence-sensitive data.
Figure 7:
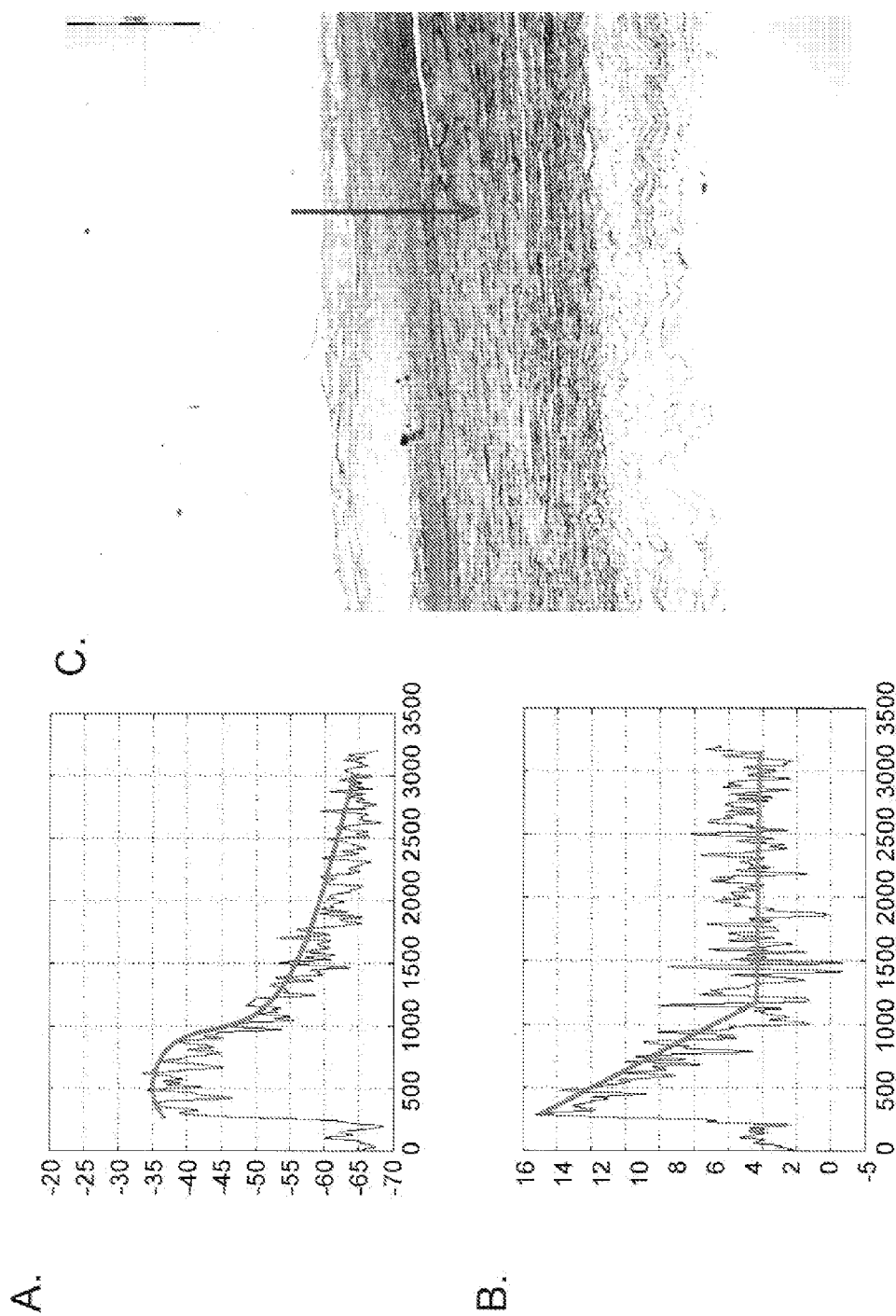
FIG. 7 shows exemplary data collected from aortic tissue using an interferometer, as embodied herein, configured to collect polarization-insensitive interferometric data and birefringence-sensitive data.

Therefore, embodiments of the invention include methods for scanning a sample 114 using an interferometer having a receiver 212 designed as described above. For example, in one embodiment, the interferometer may be initialized and data regarding a sample 114 may be obtained by collecting backscattered light from a sample and a reference arm 106, 107 to produce an optical signal. More specifically, the interferometer may be used by adjusting the optical signal such that power of the p and s polarization signal detected from the sample and reference arms 106, 107 are substantially equal, i.e., $P_1 \approx S_1 \approx P_2 \approx S_2$, by initializing the probe in the absence of scattered light in a non-reflective media or air and tuning the polarization controller 302, 402. Once initialized, a sample 114 may be scanned by adjusting the length of the reference arm 107; collecting light from a sample 114 using the initialized probe; combining collected light from the sample and reference arms 106, 107; and splitting the combined light into its p and s orthogonal states; or splitting the collected light into its p and s orthogonal states and then combining the p light of the sample and reference arms 106, 107 and the s light of the sample and reference arms 106, 107. The combined light in its p and s orthogonal states may then be detected and the interference from the polarization-insensitive signal and/or the birefringence from the birefringence-sensitive signal associated with the sample may be calculated. The interference between the reference and sample signals and/or changes in birefringence may be correlated with the health and/or make-up of the sample. For example, if a biological tissue, such as an artery is examined, the location of a plaque may be identified based on interference between the reference and the sample optical signal. At the same time, a fibrous cap associated with the plaque may be located and the size and depth of the fibrous cap may be determined based on changes in the birefringence of the optical signal from the reference and sample. The results of such analysis are illustrated in FIGS. 5-7.

In practice, digital data acquired using an interferometer as described above may be digitized and transferred to a processor 118 configured to determine the envelopes of the p and s light (env(P) and env(S), respectively). In various embodiments, the processor 118 may include a polarization-insensitive module configured to determine polarization-insensitive interference associated with the sample from env(P) and env(S) and a birefringence sensitive module configured to determine a birefringence-sensitive signal associated with the sample from env(P) and env(S). In some embodiments, the env(P) and env(S) may be determined by an individual module associated with the processor and the values for env(P) and env(S) may be transferred to the polarization-insensitive module and the birefringence-sensitive module. In other embodiments, raw data may be transferred to the polarization-insensitive module and the birefringence-sensitive module and env(P) and env(S) may be determined in the individual modules.

Figure 8A:
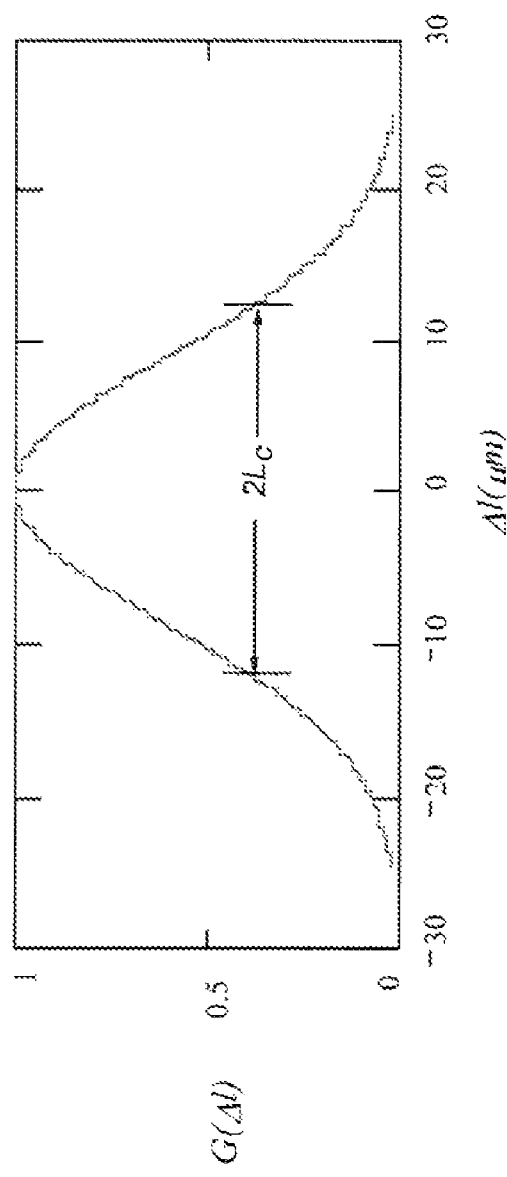
FIG. 8 shows a calculated envelope derived from exemplary interferometric data.
Figure 8B:
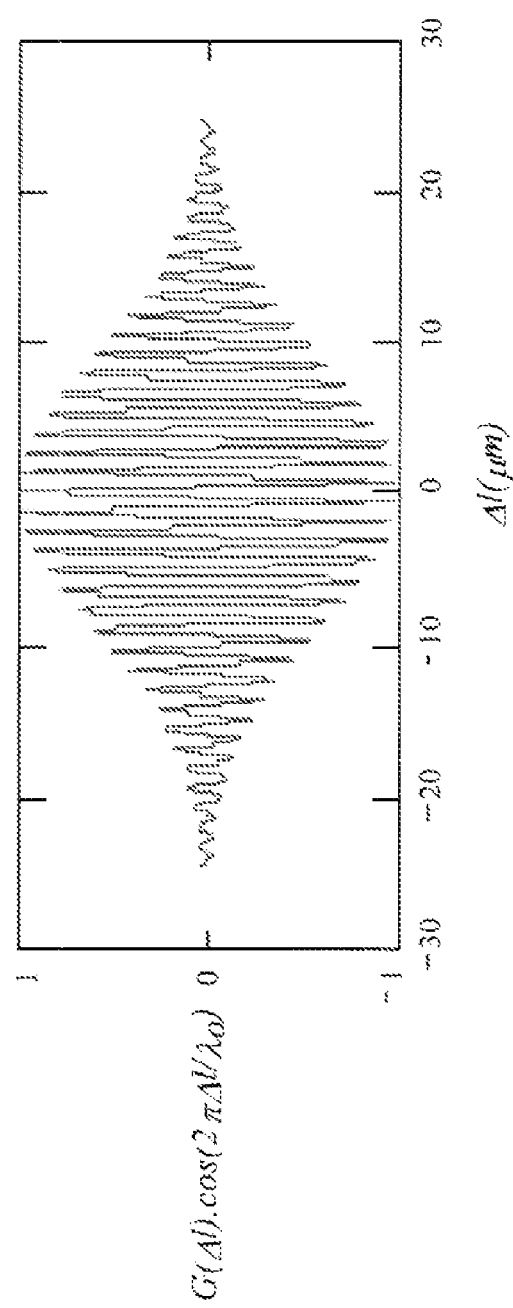

An interferometry system is designed to measure the peak of the gating function as the reference arm 107 is scanned. This is done by rectifying the interference signal $i_o$ to obtain the envelope $G(\Delta l)$ and using a peak detector the obtain the value corresponding to $\Delta l = 0$, which is the peak of the LCI signal. The envelope, or gating, function of the p-polarization and s-polarization (env(P) and env(S)) may be determined by any method known in the art. A plot of the envelope (gating) function, $G(\Delta l)$, and of the interference signal, $G(\Delta l)\cos \phi_s$, for an interferometer with a light source having center wavelength $\lambda_o = 1.3$ μm and full width half maximum (FWHM) bandwidth $\Delta\lambda = 60$ nm (coherence length $L_c = 12.4$ μm) is shown in FIGS. 8A and 8B, respectively. In FIG. 8A, the detected interference signal exhibits a maximum when the interferometer is balanced, i.e., when the path difference $\Delta l = 0$. As the system becomes increasingly unbalanced, e.g., $\Delta l \neq 0$, the interference signal exhibits maxima and minima of decreasing amplitude over a range determined by $\Delta l$. The cosine term, $G(\Delta l)\cos \phi_s$, is the real interference, and a plot of $G(\Delta l)\cos \phi_s$ for an interferometer with the 1,310 nm light source is shown in FIG. 8B. This term undergoes maxima and minima and has a $2\pi$ or 360° phase shift every time $\Delta l$ changes over a distance equal to the center wavelength of the light.

Figure 9B:
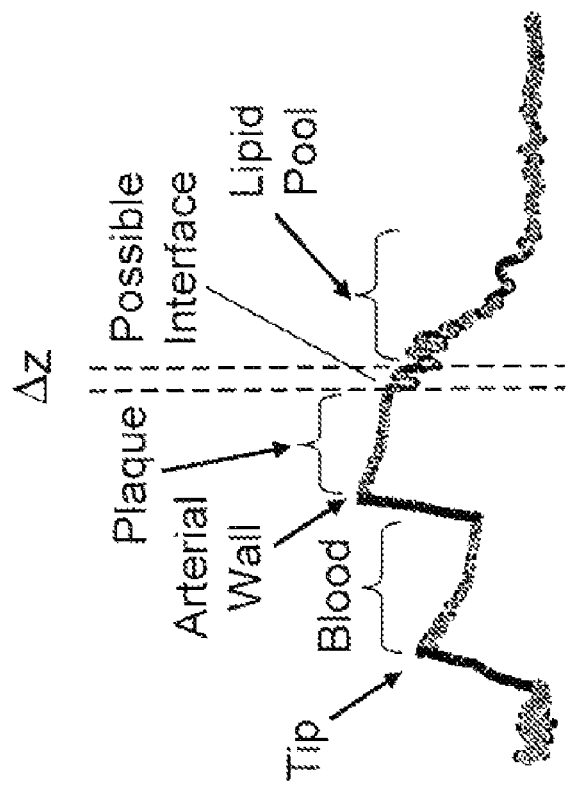
FIG. 9 shows exemplary data derived from an interferometric scan of simulated arterial tissue.
Figure 9A:
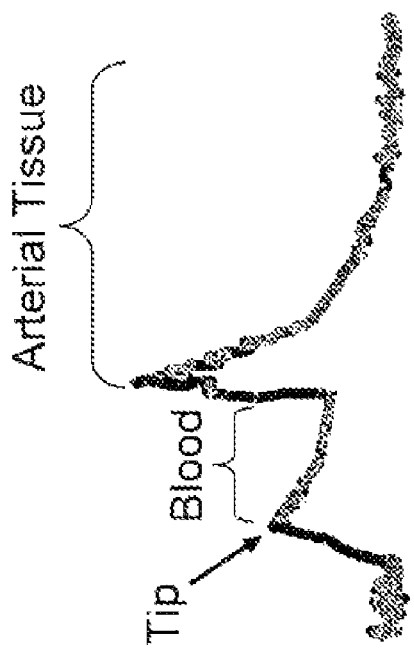

The interference signal exhibits significant amplitude only over a spatial window of approximately twice the coherence length $L_c$. As the optical bandwidth increases, the coherence length $L_c$ decreases and the spatial measurement window narrows. The existence of this gating function highlights the ability of LCI to resolve depth or optical path length. It means that, out of all the possible sensing light components that are captured by or back-scattered to the interferometer, the only component that contributes to the LCI signal is that for which the reference arm length corresponds to a depth in the sample for which the interferometer is balanced, with a resolution corresponding to the coherence length. All other signals outside of the coherence length remain as parts of the DC current, $I_s$. As the reference arm length is changed to a new value, the LCI signal obtained is one that corresponds to a new depth in the sample. By scanning the length of the reference arm over a given distance, the measurement of the peak of the gating function gives the amplitude of the profile of the LCI signal as a function of depth as illustrated in FIGS. 9A and 9B. Thus, LCI provides a means for probing objects at precisely defined locations within the object.

In an exemplary embodiment, the envelope $G(\Delta l)$ may be determined as follows. As embodied in exemplary FIGS. 1, 2 and 3, light reflected from a mirror 112 in a reference arm 107 and light reflected or scattered from depth, z, within a medium or sample under interrogation 114 from a sample arm 106 are combined to an optical coupler 300, split into their orthogonal components at a P/S splitter 304, and the light signal is detected at an optical detector 306A, 306B, 406A, 406B. The output of each detector is combined light from the sample and reference arms and includes a first electric field component, $E_r$, from light from the reference arm 107 and a second electric field component, $E_s$, from the sample arm 106, and the output current is proportional the combined electric fields. For example, in one instance, the output of the detector 306A, 306B, 406A, 406B may be proportional to the squared magnitude of the total electric field $E_t = E_r + E_s$.

The detector current $I_d$ is given by:

$$I_d = \eta |E_r + E_s|^2 = I_r + I_s + i_o(\Delta l) \quad (1)$$

where $\eta$ is the detector quantum efficiency (typically <1), $I_r = \eta E_r^* E_r^*$ is the detector current due to $E_r$ alone, $I_s = \eta E_s^* E_s^*$ is the detector current due to $E_s$ alone, and the * represents the complex conjugate. $E_r^* E_r^*$ and $E_s^* E_s^*$ represent the optical power in the reflected reference field and reflected sensing field, respectively. The quantity $i_o(\Delta l)$ is the signal of interest and represents the interference or cross-correlation signal between the two optical fields. $i_o(\Delta l)$ is given by:

$$i_o(\Delta l) = 2\sqrt{I_r I_s} \, |G(\Delta l)| \cos\phi_c \quad (2)$$

$$\text{where } |G(\Delta l)| = \exp\left[-\left(\frac{\Delta l}{L_c}\right)^2\right] \text{ and } \phi_s = \left(\frac{2\pi}{\lambda_o}\right)\Delta l$$

and where $\lambda_o$ is the center wavelength of the light source, $\Delta l$ is the optical path difference between the reference and sensing arms given by:

$$\Delta l = l_r - l_s \text{ where } l_s = nz \quad (3)$$

where $l_r$ is the path length change in the reference arm, $l_s$ is the penetration of the sensing light to depth z in the sample, n is the refractive index at the location in the sample, and $L_c$ is the coherence length of the light source which, for a light source having a Gaussian spectrum, is given by:

$$L_c = \frac{2\sqrt{\ln 2}}{\pi} \frac{\lambda_o^2}{\Delta \lambda} = 0.44 \frac{\lambda_o^2}{\Delta \lambda} \quad (4)$$

where $\Delta\lambda$ is the full width half maximum (FWHM) linewidth of the light source.

In Equation (1), the square root term represents the magnitude $I_s$ of the LCI signal which is a function of its starting depth in the sample and the reflection, transmission, and scattering properties of the sample. In particular, if the sample is a scattering material such as human tissue, $I_s$ may have an exponential dependence on z. This type of profile is predicted by scattering theory in general. The specific profile depends on the type of medium or tissue being examined. One of the main features of LCI, as applied to scattering tissues, is to experimentally obtain this profile for arbitrary tissues, whether skin for determining features such as glucose concentration, or arterial walls for the detection and characterization of vulnerable plaques.

When a medium contains several components, each component may have a different scattering coefficient, refractive index, and/or absorption coefficient. A change in the profile will occur at each interface, depending on the value of these parameters on each side of the interface. When the two media have significantly different scattering characteristics, the profile may exhibit a measurable amplitude step. FIG. 9A depicts an LCI profile of an arterial wall in a set-up containing blood between the probe tip and the arterial wall simulated by a sheet of rubber. The blood is a scattering medium, and the left portion of the profile is based on the blood, while the arterial wall (rubber sheet) is more highly scattering than the blood and therefore the profile exhibits higher relative amplitude LCI. To the extent that enough light has penetrated through the blood to produce a measurable LCI for the rubber, one sees a larger LCI for the rubber, as indicated by the step in the sketch. FIG. 9B represents the LCI signal for a calcified plaque on an arterial wall with a lipid pool between the plaque and the arterial wall, looking through blood. In the profile depicted, the step increase due to the higher scattering coefficient of the plaque and a step decrease resultant from the lower scattering of the lipid pool may readily be observed. It will be appreciated that by then measuring from the beginning of the hump or step corresponding to the plaque to the beginning of the portion of the signal corresponding to the lipid pool, a measure of the thickness of the plaque cap may be ascertained.

The accuracy of such a measurement is determined by the accuracy with which the transition can be detected, for example, as depicted in FIG. 9B, the transition from the calcified plaque cap to lipid pool. Unfortunately, the transition may not be easily detected, with sufficient accuracy, by looking at only the amplitude of the interferometric signal $i_o$. Moreover, there may be subtle changes due to some possible other interfaces that cannot be readily measurable from the amplitude information alone. Therefore, in various embodiments of the invention, such changes may be detected from the phase information in the LCI signal. In fact, any change in material property, whether it is refractive index, absorption, scattering (which can be treated as a change of absorption or reflection) will affect the phase of the interferometric signal, $i_o$. Therefore, if a change in material property is abrupt at a given location, the change may be represented as an abrupt phase shift in the signal at the location. For example, as a depth scan is conducted, the phase of the interferometric signal is expected to vary by a predictable amount depending medium. When a different medium is encountered exhibiting different scattering properties a significant change in the properties beyond that expected will be encountered. Therefore, the thickness of the various layers of a vulnerable plaque may be ascertained by observing such changes in a layered structure and recording their positions. In one embodiment, abrupt variations in phase and or index of refraction the order of about 0.1% per micron of scan distance are considered as likely changes in medium.

A calculation of the high sensitivity of the phase measurement can be shown for the simple case of only a small refractive index change in the transition from one medium to another over a small distance $\Delta z$ (FIG. 9B). From Equation 3, the phase angle $\phi_s$ of the LCI signal, for a depth in the sample determined by $l_r$ for an interface at depth nz (which is $l_s$) is written as:

$$\phi_s = \left(\frac{2\pi}{\lambda_o}\right)\Delta l = \left(\frac{2\pi}{\lambda_o}\right)(l_r - nz) \quad (5)$$

Moreover, the phase, $\phi_s$, (Equations (2), (5) of the interference signal, $i_o$, changes by $2\pi$ (from a maximum to a minimum then to another maximum) as $\Delta l$ varies from 0 to $\lambda_o$. Therefore, a small change in $\Delta l$ results in a large phase change. It will be further appreciated that the phase of the interference signal, $i_o$, is highly sensitive to small changes of optical properties of the mediums, such as refractive indices, or depth z. Thus, while moderate to large changes may readily be observed by measuring the magnitude of the envelope $G(\Delta l)$, small changes are best detected by measuring the phase $\phi_s$ of the interference signal $i_o$. It will be further appreciated that, for certain applications, all the desired information is contained in the range from 0 to $2\pi$. For values of $\Delta l > \lambda_o$, the interference signal $i_o$ is repetitive. Thus, in such applications, the range from 0 to $2\pi$ as indicated in FIG. 8 is a range for which the desired information can be measured without ambiguity. However, if the coherence length $L_c$ is short enough that the amplitude difference between the main peak and secondary peaks is measurable, or if a means is provided to record a particular point of the interference signal, then phase measurement beyond $2\pi$ may be realized by counting the fringes (the number of equivalent points traversed) starting from that point.

Therefore, there are two types of information, which can be derived from the interference signal $i_o$ the envelope $G(\Delta l)$, or its peak $G(\Delta l=0)$, which may represent scattering, reflection, and absorption; and the more sensitive changes in phase, or $\cos \phi_s$, due to small optical property changes in the specimen under study. In order to make any such measurements, it is first preferable to separate the DC components $I_r$ and $I_s$ from $G(\Delta l)$ and $\cos \phi_s$ in the interferometric signal $i_o$ described in Equation (5).

In various embodiments of the invention, only the magnitude of the interference may be measured or only the phase of the interference may be measured. In certain embodiments, both the magnitude and the phase of the interference may be measured. Systems which are capable of measuring both the magnitude and phase of the interference are described in U.S. patent application Ser. No. 10/845,853, entitled "Low Coherence Interferometry Utilizing Magnitude", and U.S. patent application Ser. No. 10/845,849, entitled "Low Coherence Interferometry Utilizing Phase", the contents of each are hereby incorporated by reference in their entireties.

In various embodiments, the env(P) and env(S) for each output signal from the P/S splitter 304, 404 may be detected and applied in pairs, i.e. P1 and P2, S1 and S2 to balanced detectors 310, 311, 410, 411 whose output is used to determine env(P) and env(S) as described above. The combination of env(P) and env(S) may provide the polarization-insensitive interferometric signal ($LCI_{P1}$) which can be determined by a polarization-insensitive module as follows:

$$LCI_{P1} = 20 \log \sqrt{env(P)^2 + env(S)^2} (dB) \quad (6)$$

In various other embodiments, the birefringence or degree of polarization of a sample may also be characterized. A value of a birefringence sensitive interferometric signal ($LCI_{BS}$) may be determined by a birefringence sensitive module as follows:

$$LCI_{BS} = 20 \log\left(\frac{env(P)}{env(S)}\right)(dB) \quad (7)$$

Without wishing to be bound by theory, the polarization insensitive LCI signal ($LCI_{P1}$) for a sample may provide interferometric characterization of a sample in which polarization changes caused by propagation of light through waveguides associated sample and references arms has been effectively eliminated. Therefore, the $LCI_{P1}$ represents only interference caused by the sample. In the same way, birefringence caused by propagation of light through waveguides of the sample and reference arms has been effectively eliminated, so a measurement of birefringence associated with a sample ($LCI_{BS}$), can be determined. In either case, the determination of $LCI_{P1}$ and $LCI_{BS}$ provides an improved measurement of interference caused by a sample. $LCI_{BS}$ provides an otherwise unattainable measure of birefringence from the sample.

FIGS. 5-7 show exemplary data LCI collected from human aortic tissue samples. In FIG. 5, panel C shows a histological section of aortic tissue containing a thick cap fibroatheroma. A fibrous cap, FC, containing collagen and a necrotic core, NC, not containing collagen can be readily discerned from this histological section. Panel A shows a polarization-insensitive interferometric signal obtained by scanning the tissue of Panel C as illustrated by the red arrow. The optical pathlength (microns) of the scan is provided on the X-axis and represents depth within the scanned tissue and the Y-axis represents the polarization insensitive envelope detected optical power (dB). The fibrous cap, FC, can be identified by the increase in amplitude of the polarization insensitive envelope (illustrated by red lines) and the exponential decrease of the signal is associated with the necrotic core (illustrated by red lines). Panel B shows the birefringence-sensitive signal associated with the tissue sample of Panel C. The optical pathlength (microns) is provided on the X-axis and aligned so as to correspond with the optical pathlength of Panel A. The Y-axis is the Log of the polarization ratio (dB) or birefringence signal. Panel B shows an abrupt change in birefringence as the scan moved out of the highly birefringent, collagen containing fibrous cap, FC, and into the low birefringent, low collagen containing necrotic core, NC. Similarly FIGS. 6 and 7 Panels A show the polarization-insensitive interferometric data, with X and Y axis as described above, and Panels B show the birefringence-sensitive data, with X and Y axis as described above, collected from human aortic tissue with a histological section shown in panels C, with the scan direction provided by the red arrow. As illustrated in FIG. 6, comparing the polarization-insensitive interferometric data with the birefringence-sensitive data shows the presence of a thinner fibrous cap and necrotic cap, and healthy tissue or tissue exhibiting adaptive minimal thickening but not having a fibrous cap, as shown in FIG. 7, can be readily discerned.

The polarization insensitive module and the birefringence sensitive module may be implemented within a processor as hardware, software, or combinations thereof. For embodiments where the modules are implemented in software, the modules may be implemented using any suitable computer language including but not limited to C, C++, Java, JavaScript, Visual Basic, VB Script, Perl, Delphi, and the like, and may be embodied permanently or temporarily in any type of machine, component, physical or virtual equipment, storage medium, or propagated signal capable of delivering instructions to a device. The modules may be stored on a computer-readable medium such as, for example, a disk, device, propagated signal, or combinations thereof, such that when a computer reads the medium, the functions described herein are performed. According to various embodiments, the modules may be installed on separate, distinct systems, and different functional aspects of the modules may be installed on separate, distinct devices. In some embodiments, the functionality of the modules may be combined into a single module.

The receiver 212 of interferometer systems described herein may include optical couplers, amplifiers, polarization controllers, optical splitters, optical circulators, detectors, digital acquisition boards, processors, etc. coupled to one another in a multitude of arrangements.

According to various embodiments of the system, the light source 100 may be, for example, a laser, one or more diodes, a white light source, EM wave sources in different frequency and wavelength ranges, superfluorescent optical fibers, etc. The laser may be a mode locked Ti:Al$_2$O$_3$ laser. The diode may be a superluminescent diode (SLD), a light emitting diode (LED) such as an edge emitting diode, multiple quantum well emitting diodes, etc. The light source may include one or more light sources having the same or different wavelengths, or may include one or more quantum well devices formed on a single substrate to provide light at multiple wavelengths. The light source may be capable of penetrating a sample and providing torturous as well as ballistic light trajectories in the sample. The source light emitted by the light source may include but is not limited to low coherence light or multiple low coherent light having different center wavelengths whose outputs have been combined. The source light may be emitted at near infrared and infrared wavelength, have short coherence length and may have high irradiance for penetrating deep into the sample. The low coherence source light may have wavelengths from about 600 to about 1800 nm. The penetration of the light into the sample may vary depending on the wavelength and power of the source light used, the use of optical circulators, coupling losses, component attenuation light, the type of sample being scanned, etc.

An optical coupler or splitter 102, 109, 300, 400 may be embodied as, for example, lightsplitter cubes, light splitter plates, evanescent-mode couplers, fiber couplers, prisms, etc. The splitter may be operative to both split the optical power of the light source for propagation through the reference and sample arms of the interferometer and combine backscattered light from the sample with light from the reference arm. The optical power may be split equally or unequally. For example, according to various embodiments, the splitter 102, 109, 300, 400 is operative to split the optical power substantially equally between a sample and reference arm 106, 107. In other embodiments, the splitter 102, 109, 300, 400 may be operative to split the optical power such that about 5% of the light is delivered to the reference arm 107 and about 95% of the light is delivered to one or more sample arms 106. According to various embodiments, the interferometer may include additional splitters 109 operative to further split the light to be delivered to the sample arms 106.

The sample arm 106 may include a waveguide, an optical fiber, a free space structure, or combinations thereof. The sample arm 106 may be operative to propagate low coherence source light 100 to a sample 114 and collect backscattered source light from the sample 114. The interferometer may also include a modulator and probe associated with the sample arm 106. The interferometer may be operative to detect the frequency of the modulator. The probe may be operative to reflect the source light such that a portion of the source light is used to provide reference light and another portion of the source light is used to irradiate the sample 114. The reference light and backscattered light from the sample may be collected and propagated by the probe. Although only one sample arm 106 is shown in FIG. 2, it is understood that the interferometer may comprise any number of sample arms.

The reference arm 107 may include a waveguide, an optical fiber, a free space structure, or combinations thereof. The reference arm 107 may also include one or more reflectors. The reference arm 107 may be operative to produce reference light from source light that is within the coherence length of the light backscattered from the sample and received by a sample arm. The signal from the reference arm 107 represents light that is the same coherence length as the light of at least one sample arm 106 that has not been scattered by the sample. The interferometer may also comprise a delay compensator that is associated with the reference arm 107. Although only one reference arm 107 is shown in FIG. 2, it is understood that the interferometer may also comprise any number of reference arms.

The interferometer also includes optical fibers. The optical fibers may be single mode (SM) optical fibers, polarization maintaining (PM) fibers, fiber optic cable, etc. In various embodiments, single mode fiber may be used because it may propagate and collect a single transverse spatial mode optical light that may be focused to a minimum spot size (the diffraction limit). A single mode optical fiber may consist of a core, a cladding, and a jacket. The core of the fiber, through which the light is guided, may be any suitable size, for example form about 5 to about 9 microns in diameter. The core of the fiber may be surrounded by a glass cladding in order to facilitate light guiding and/or add mechanical strength to the fiber. In other embodiments, polarization maintaining fibers may be used to provide a better signal to noise ratio. The waveguides and channels which comprise a portion of the interferometer may be single mode channels and may be capable of maintaining light polarization.

In various embodiments of the system, the interferometer may utilize light that travels through a catheter or guidewire system by mans of optical fibers. The optical fibers may direct transmitted light to an area that may or may not contain a plaque, lesion, or malformation and collect light reflected back from that area. The reflected light may then be used to determine the size, thickness and/or density of a plaque, lesion, or malformation.

In various embodiments, the interferometer may utilize light that travels through the optical fibers as a set of modes whose number and geometry may be determined by the propagating wavelength, the size of the fiber core, and the index difference between the optical fiber core and its cladding material. Light may propagate in an optical fiber in the form or rays bouncing laterally at the boundary between the core and cladding material by virtue of total internal reflection as the wave propagates along the fiber axis. Unlike open space propagation, these bounces may occur only at discrete angles, characterized by a set of numbers, one for each mode. The number of modes may be determined by the value of a "characteristic frequency" V, defined as $V=(2\pi a/\lambda)\sqrt{n_1^2-n_2^2}$, where (a) is the fiber core radius, ($\lambda$) is the wavelength of the light, ($n_1$) and ($n_2$) are the respective indexes of refraction of the fiber core and cladding material. In some embodiments, the interferometer may only utilize the single and lowest propagating mode. Mathematically, this requires V to be <2.4 for that particular wavelength.

The interferometer may further include a light collector that gathers backscattered light from the sample 114 illuminated by light from the light source 100. The light collector may comprise a lens, an optical fiber, a mirror, a waveguide, and combinations thereof. In various embodiments, a light collector may also provide source light to the sample and function as a transceiver.

The detector 306A, 306B, 406A, 406B may be considered either a portion of the interferometer or the receiver 212, and may be operative to measure the intensity of interference between backscattered light from the sample arm 106 and light from the reference arm 107. The detector 306A, 306B, 406A, 406B may generate a signal that is proportional to the amplitude or intensity of interference between the backscattered light from the sample and light from the reference arm at the optical path length that have been coupled together by, for example, a coupler or a light combiner 300, 400. The detector 306A, 306B, 406A, 406B may be a single photodetector, dual-balanced detectors, or an array of photo-detectors. In embodiments where a light source 100 or multiple sources operating at several wavelengths simultaneously are used, the detector may include an array of photodetectors having a photodetector for each wavelength, and a grating or similar light dispersion element positioned in front of the array in order to distinguish the reflected signal corresponding to each one of the different wavelengths. Alternatively, the detector 306A, 306B, 406A, 406B may be a single photodetector when the system includes one or more additional delays that are operative to separate various signals.

For embodiments where the backscattered light from the sample is collected by a light collector such as an optical fiber, the collected light may be coupled with light from a reference arm at the same optical path length, and the combined light may applied to a photodetector that may convert the intensity of interference to a proportional current-varying electrical signal. The current-varying electrical signal from the photodetector may then be converted to a voltage-varying signal by a trans-impedance amplifier or other suitable devices that comprise a portion of the system. The output of the detectors 306A, 3096B, 406A, 406B may be an analog signal, and the analog signal may be converted to a digital signal. The output signal may then be used to determine the absorption, $\mu_a$ and diffusion D (inverse scattering) coefficients of the sample through a function. The absorption, $\mu_a$ and diffusion D coefficients thus determined may then be correlated with, for example, the concentration of an analyte in the sample or a type of material present in the sample.

The system may also include a processor 118. In such a processor 118, the polarization insensitive module and the birefringence sensitive module may make up a portion of the interferometer or the receiver 118, or may be separate from and in communication with the interferometer or receiver 118. The processor 118 may be configured to provide an output that is proportional to the interference measured between the sample and the reference light. In some embodiments, the processor 118 may be configured to modulate the light signal in the sample arm and/or the reference arm 106, 107 by activating or adjusting one or more components such as, for example, optical couplers 300, 400, polarization controllers 302, 402, VOA 22, stretchers 222, waveguides, detectors 306A, 306B, 406A, 406B, light sources 100, and the like that make-up the interferometer system.

The interferometer system described herein may further include an output device, such as, for example, a video monitor, printer, digital output device, and the like or combinations thereof.

Although the sample 114 illustrated in FIG. 2 is a biological tissue in a saline surrounding, it will be appreciated that the sample can be any type of sample. Also, for samples that are biological tissue samples, the tissue can be in a live human being.

While several embodiments of the invention have been described herein by way of example, those skilled in the art will appreciate that various modifications, alterations, and adaptions to the described embodiments may be realized without departing from the spirit and scope of the invention defined by the appended claims.

What is claimed is:

1. An apparatus comprising:
a first polarization controller;
a polarization splitter optically coupled to the first polarization controller;
an optical coupler optically coupled to one of the following:
    the first polarization controller; and
    the polarization splitter;
first and second detectors optically coupled to one of the following:
    the polarization splitter; and
    the optical coupler; and
a balanced detector electrically connected to at least one of the first and second detectors; and
a second polarization controller optically coupled to the optical coupler.

2. The apparatus of claim 1, further comprising a second polarization splitter optically coupled to the second polarization splitter.

3. The apparatus of claim 2, further comprising third and fourth detectors optically coupled to the second polarization splitter.

4. The apparatus of claim 3, further comprising a second balanced detector electrically connected to the second and fourth detectors.

5. The apparatus of claim 1, further comprising a second polarization splitter optically coupled to the first polarization controller.

6. The apparatus of claim 5, further comprising third and fourth detectors optically coupled to the second polarization splitter.

7. The apparatus of claim 6, wherein at least one of the third and fourth detectors is electrically connected to the balanced detector.

8. The apparatus of claim 6, further comprising a second balanced detector electrically connected to at least one of the third and fourth detectors.

9. The apparatus of claim 8, wherein at least one of the third and fourth detectors is electrically connected to the balanced detector.

10. An apparatus comprising:
a polarization controller;
a polarization splitter optically coupled to the polarization controller;
an optical coupler optically coupled to one of the following:
    the polarization controller; and
    the one polarization splitter;

first and second detectors optically coupled to one of the following:
the polarization splitter; and
the optical coupler; and
a balanced detector electrically connected to at least one of the first and second detectors; and
third and fourth detectors, wherein at least one of the third and fourth detectors is electrically connected to the balanced detector.

11. An apparatus comprising:
a polarization controller;
a first polarization splitter optically coupled to the polarization controller;
an optical coupler optically coupled to one of the following:
the polarization controller; and
the first polarization splitter;
first and second detectors optically coupled to one of the following:
the first polarization splitter; and
the optical coupler; and
a balanced detector electrically connected to at least one of the first and second detectors; and
a second polarization splitter optically coupled to the optical coupler.

12. The apparatus of claim 11, further comprising a second optical coupler optically coupled to the second polarization splitter.

13. The apparatus of claim 12, wherein the second optical coupler is optically coupled to the first polarization splitter.

14. The apparatus of claim 12, further comprising third and fourth detectors optically coupled to the second optical coupler.

15. The apparatus of claim 14, further comprising a second balanced detector electrically connected to at least one of the third and fourth detectors.

16. An apparatus comprising:
a polarization controller;
a first polarization splitter optically coupled to the polarization controller;
an optical coupler optically coupled to one of the following:
the first polarization controller; and
the one polarization splitter;
first and second detectors optically coupled to one of the following:
the first polarization splitter; and
the optical coupler; and
a balanced detector electrically connected to at least one of the first and second detectors; said apparatus further comprising an optical circulator optically coupled to at least one of the following:
the optical coupler; and
the polarization splitter; and
a second optical circulator optically coupled to at least one of the following:
the optical coupler; and
a second polarization splitter which is optically coupled to the optical coupler.

17. A system comprising:
an interferometer;
an apparatus optically coupled to the interferometer, wherein the apparatus comprises:
a polarization controller;
a polarization splitter optically coupled to the polarization controller;
an optical coupler optically coupled to one of the following:
the polarization controller; and
the polarization splitter;
first and second detectors optically coupled to one of the following:
the polarization splitter; and
the optical coupler; and
a balanced detector electrically connected to at least one of the first and second detectors;
a first optical circulator optically coupled to a reference arm of the interferometer; and
a second optical circulator optically coupled to a sample arm of the interferometer.

18. The system of claim 17, wherein the first optical circulator is optically coupled to one of the following:
the optical coupler; and
the polarization controller.

19. The system of claim 17, wherein the second optical circulator is optically coupled to one of the following:
the optical coupler; and
a second polarization splitter which is optically coupled to the optical coupler.

20. A method for determining a characteristic of a sample using an interferometer, the method comprising:
illuminating the sample via the interferometer;
illuminating a mirror associated with the interferometer;
collecting backscattered light from the sample to provide a first reflected component;
collecting reflected light from the mirror to provide a second reflected component;
controlling polarization of the first and second reflected components;
determining a p-polarization component and a s-polarization component for each of the first and second reflected components;
determining a difference between the p-polarization components and a difference between the s-polarization components; and
determining a birefringence sensitive signal based on the difference between the p-polarization components and the difference between the s-polarization components.

21. The method of claim 20, wherein controlling the polarization comprises controlling the polarization such that, when the sample is absent:
the p-polarization component and the s-polarization component of the first reflected component are of equal intensity; and
the p-polarization component and the s-polarization component of the second reflected component are of equal intensity.

22. The method of claim 20, wherein controlling the polarization comprises controlling an optical path length in the interferometer.

23. The method of claim 20, wherein determining the p-polarization component and the s-polarization component for each of the first and second reflected components comprises:
optically combining the first and second reflected components;
controlling the polarization of the combined components; and
splitting the first and second reflected components into their respective p-polarization and s-polarization components.

24. The method of claim 20, wherein determining the p-polarization component and the s-polarization component for each of the first and second reflected components comprises:

controlling the polarization of the second reflected component; and splitting the first and second reflected components into their respective p-polarization and s-polarization components.

25. The method of claim 20, wherein determining a difference between the p-polarization components and a difference between the s-polarization components comprises generating electrical signals representative of the respective p-polarization and s-polarization components of the first and second reflected components.

26. The method of claim 20, wherein determining a difference between the p-polarization components and a difference between the s-polarization components comprises:

optically combining the p-polarization components of the first and second reflected components;

optically combining the s-polarization components of the first and second reflected components; and generating electrical signals representative of the respective p-polarization and s-polarization components of the first and second reflected components.

27. The method of claim 20, further comprising determining a characteristic of the sample based on the birefringence sensitive signal.

28. The method of claim 20, further comprising determining a polarization-insensitive signal associated with the sample.

29. The method of claim 28, wherein determining the polarization insensitive signal comprises:

determining a p-envelope based on the difference between the p-polarization components of the first and second reflected components; and determining a s-envelope based on the difference between the s-polarization components of the first and second reflected components.

30. The method of claim 29, wherein the p-envelope and the s-envelope are determined over a range of optical pathlengths by adjusting a pathlength of the interferometer.

31. The method of claim 29, wherein determining the polarization-insensitive signal comprises determining a value for the expression:

$$20 \log \sqrt{\text{env}(P)^2 + \text{env}(S)^2} \, (\text{dB}).$$

32. The method of claim 20, wherein determining the birefringence sensitive signal comprises determining a value for the expression:

$$20 \log \left( \frac{\text{env}(P)}{\text{env}(S)} \right) (\text{dB}),$$

wherein env(P) is determined based on the difference between the p-polarization components of the first and second reflected components, and wherein env(S) is determined based on the difference between the s-polarization components of the first and second reflected components.

* * * * *